US008673280B2

(12) United States Patent
Leino et al.

(10) Patent No.: US 8,673,280 B2
(45) Date of Patent: Mar. 18, 2014

(54) PHARMACEUTICAL COMPOSITION FOR INTRACELLAR ACIDIFICATION WITH CIS-UROCANIC ACID

(71) Applicant: BioCis Pharma Oy, Turku (FI)

(72) Inventors: Lasse Leino, Merimasku (FI); Jarmo Laihia, Lieto (FI)

(73) Assignee: BioCis Pharma Oy, Turku (FI)

( * ) Notice: Subject to any disclaimer, the term of this patent is extended or adjusted under 35 U.S.C. 154(b) by 0 days.

(21) Appl. No.: 13/651,555

(22) Filed: Oct. 15, 2012

(65) Prior Publication Data

US 2013/0041006 A1 Feb. 14, 2013

Related U.S. Application Data

(63) Continuation of application No. 10/534,988, filed as application No. PCT/FI2004/000109 on Mar. 1, 2004, now Pat. No. 8,313,738.

(30) Foreign Application Priority Data

Mar. 14, 2003 (FI) .................................. FI20030379

(51) Int. Cl.
*A61K 31/4172* (2006.01)
*C07D 233/00* (2006.01)

(52) U.S. Cl.
USPC ..................... 424/78.04; 424/78.05; 514/885; 514/912

(58) Field of Classification Search
None
See application file for complete search history.

(56) References Cited

U.S. PATENT DOCUMENTS

| | | | | |
|---|---|---|---|---|
| 4,794,106 | A | 12/1988 | Takashima et al. | ........... 514/179 |
| 5,494,676 | A | 2/1996 | Stab et al. | ...................... 424/401 |
| 5,686,100 | A | 11/1997 | Wille et al. | .................... 424/449 |
| 5,843,979 | A * | 12/1998 | Wille et al. | .................... 514/408 |
| 5,912,010 | A | 6/1999 | Wille et al. | .................... 424/449 |
| 5,995,869 | A | 11/1999 | Cormier et al. | ................. 604/20 |
| 6,028,098 | A | 2/2000 | Goodman et al. | ............ 514/427 |
| 6,153,176 | A | 11/2000 | Kaleta et al. | ..................... 424/60 |
| 6,310,067 | B1 * | 10/2001 | Ogata et al. | ............. 514/253.09 |
| 6,372,199 | B1 | 4/2002 | Gers-Barlag et al. | ........... 424/59 |
| 2002/0111362 | A1 | 8/2002 | Rubinfeld | ...................... 514/283 |

FOREIGN PATENT DOCUMENTS

| | | |
|---|---|---|
| DE | 41 21 030 | 1/1992 |
| DE | 41 22 497 | 1/1993 |
| EP | 0 467 116 | 1/1992 |
| EP | 0 612 525 | 8/1994 |
| WO | WO 02/07520 | 1/2002 |

OTHER PUBLICATIONS

M Matsui, T Tashiro. English Translation of "Protective Effect of Urocanic Acid Eye-Drops to the Ocular Inflammation Induced by the Ultraviolet Radiation." The Japanese Opthalmological Society (Nihon Ganka Gakkai Zasshi), vol. 71, No. 6, 10 Jun. 1967, pp. 1-10.*
Murahata et al., "Effect of pH on the Production of Irritation in a Chamber Irritation Test," 18 *J. Am. Acad. Dermatol.* 62 (1988).
Antoine et al., "pH Influence of Surfactant-induced Skin Irritation," 37 *Derm. Beruf. Umwelt.* 96 (1989).
Berner et al., "The Relationship between pKa and Skin Irritation for Series of Basic Penetrants in Man," 15 *Fund. Applied. Toxic.* 760 (1990).
Bucher et al., "Irritant Actions of Unphysiological pH Values. A Controlled Procedure to Test for Topical Irritancy," 9 *Agents Actions* 124 (1979).
McKinney et al., "Irritant Action of Binary Soaps Mixtures on Skin," *Oil & Soap* 198 (1940).
Bettley et al., "The Irritant Effect of Soap upon the Normal Skin," 72 *Br. J. Dermatol.* 67 (1960).
Korting et al., "Influence of Skin Cleansing Preparation Acidity on Skin Surface properties," 13 *Int. J. Cosmet. Sci.*, 91 (1991).
Guillot et al., "Evaluation of the Cutaneous-Irritation Potential of 56 Compounds," 20 *Fd. Chem . Toxic.* 563 (1982).
Oestreicher, "Detergents, Bath Preparations, and Other Skin Cleansers," 6 *Clin. Dermatol.* 29 (1988).
Singh et al., "Comparative Measurement of Irritant Properties of Toilet bar Soaps on Human Skin," 56 *Indian J. Dermatol. Venereol. Leprol.* 67 (1990)
Cho et al., "Effect of the pH in Soaps on Skin Irritation," 4 *Korean J. Invest. Dermatol*, 124 (1997).
Goosens, "Allergy and Hypoallergenic Products", Chapter 53 of *Handbook of Cosmetic Science and Technology* ( $3^{rd}$ ed., Barel et. al. eds., 2009).
Van Der Valk et al., "Skin Irritancy of Surfactants As Assessed by Water Vapor Loss Measurements," 82 *J. Invest. Dermatol.* 291 (1984).
Johansen, "Fragrance Contact Allergy," 4 *Am. J. Clin. Dermatol.* 789 (2003).
Timm-Knudson at al., "Allergic Contact Dermatitis to Preservatives," 18 *Dermatol. Nursing* 130 (2006).
Paye, "Mechanisms of Skin Irritation by Surfactants and Anti-Irritants for Surfactant-Based Products," chapter 43 of *Handbook of Cosmetic Science and Technology* ( $3^{rd}$ ed., Barel et. al. eds., 2009).
Lakshmi et al., "Irritancy Ranking of 31 Cleansers in the Indian Market in a 24-h Patch Test," 30 *Int. J. Cosmet. Sci.* 277 (2008).
Halvarsson et al., "Increasing Quality of Life by Improving the Quality of Skin in Patients with Atopic Dermatitis," 29 *Int. J. Cosmet. Sci.* 69 (2007).
Burobin et al., "Biological Activity of Urocanic Acid," 31 *Voprosy Meditsinskoi Khimii* 102 (1985) with Translation.

(Continued)

*Primary Examiner* — Frederick Krass
*Assistant Examiner* — Isaac Shomer
(74) *Attorney, Agent, or Firm* — James C. Lydon

(57) ABSTRACT

A pharmaceutically acceptable agent able to acidify the cell cytoplasm for the manufacture of a pharmaceutical composition useful for causing immunosuppression in a person or animal, where an effective amount of the agent is administered in an essentially non-dissociated form to the person or animal, and where the agent is admixed with a carrier to adjust the pH of the composition to the pH range 6.1 to 7.0. A pharmaceutical composition is also disclosed.

3 Claims, 9 Drawing Sheets

(56) References Cited

OTHER PUBLICATIONS

Mohammad et al, "Invited Review: Urocanic Acid Photochemistry and Photobiology," 69 *Photochemistry and Photobiology*. 115 (1999).

Holmes, "Paclitaxel combination Therapy in the Treatment of Metastatic Breast Cancer," 23 *Seminars in Oncology* 29 (1996).

Roberts, "A Nitrogen-15 Nuclear Magnetic Resonance Study of the Acid-Base and Tautomeric Equilibria of 4-Substituted Imidazoles and Its Relevance to the Catalytic Mechanism of a-Lytic Protease," 104 *J.Am.Chem.Soc*. 3945 (1982).

Tew et al., "Ethacrynic Acid and Piriprost as Enhancers of Cytotoxicity in Drug Resistant and Sensitive Cell Lines," 48 *Cancer Research* 3622 (1988).

Schultz et al., "Inhibitors of Glutathione S-transferases as Therapeutic Agents," 26 *Advanced Drug Delivery Reviews* 91(1997).

Mastitis. The American Heritage Stedman's Medical Dictionary (2002). Retrieved Sep. 11, 2006 from xreferplus. http://xreferplus.com/entry/2785531.

Granstein, "Psoriasis: Further Evidence of a Key Role for Leukocytes," 98 *J. Clin, Invest*. 1695-96 (1996).

Ben-Basset et al., "Inhibitors of Tyrone Kinases in the Treatment of Psoriasis," 6 *Current Pharmaceutical Design* 933-942 (2000).

Baranda et al., "Correlation Between pH and Irritant Effect of Cleansers Marketed for Dry Skin," 41 *Int'l J. Dermatology* 494 (2002).

Purdue University, "pH, pOH and Ka" http://chemed.chem.purdue.edu/genchem/topicreview/bp/ch17/ph.php, Feb. 23, 2006 (as of internet archive) 9 pages.

Mohammad et al., "Urocanic Acid Photochemistry and Photobiology," 6 Photochem. & Photobiol. 115 (1999).

Prater, "Immunotoxicity of Dermal Permethrin and Cis-Urocanic Acid: Effects of Chemical Mixtures in Environmental Health," PhD Thesis, Virginia Polytechnic Institute and State University (Mar. 8, 2002).

Stephenson, "Inflammation", General and Systemic Pathology 199 (J.C.E. Underwood and SS Cross eds. $5^{th}$ ed. 2009).

Yuan et al., "Effects and Mechanisms of Aloperine on 2,4-Dinitrofluorobenzene-induced Allergic Contact Dermatitis in BALB/c Mice," 629 *European J. Pharmacy* 147 (2010).

Guymer et al., "Urocanic Acid in Allotransplantation," 22 *Transplantation Proceedings* 2119 (1990).

Lee et al., "Reactive Oxygen Species Removal Activity of Davallialactone Reduces Lipopolysaccharide-induced Pulpal Inflammation Through Inhibition of the Extracellular Signal-regulated Kinase ½ Nuclear Factor Kappa B Pathway", 37 *J. Endod*. 491 (2011) (Abstract).

Manukyan et al., "Interleukin-10 Protects the Ischemic Heart From Reperfusion Injury via the STAT3 Pathway," 150 *Surgery* 231 (2011).

Minneci et al., "Increasing the Efficacy of Anti-Inflammatory Agents Used in the Treatment of Sepsis," 22 *Eur. J. Clin. Microbiol. Infect. Dis*. 1 (2003).

Oesterwitz et al., "Inhibition of Rat Heart Allograft Rejection by a PUVA Treatment of the Graft Recipient," 3 *Transplant Int*. 8 (1990).

Pech et al., "Combination Therapy of Tacrolimus and Infliximab Reduces Inflammatory Response and Dysmotility in Experimental Small Bowel Transplantation in Rats," 93 *Transplantation* 249 (2012).

Rinaldi et al., "Effect of cis-Urocanic Acid on Bovine Neutrophil Generation of Reactive Oxygen Species," 89 *J. Dairy Sci*. 4188 (2006).

Salama et al., "Advances in Drug Delivery: Is Triple Therapy the Future for the Treatment of Chronic Obstructive Pulmonary Disease?", 12 *Expert Opin. Pharmacother*. 1913 (2011).

Thomson, "Chronic Inflammation of the Peritoneum and Vagina," 50 *J. Reproductive Med*. 507 (2005).

Bannerman et al., "Effects of Intramammary Infusion of cis-Urocanic Acid on Mastitis-associated Inflammation and Tissue Injury in Dairy Cows," 70 *Am. J. Vet. Res*. 373 (2009).

Chainani-Wu et al., "High-dose Curcuminoids Are Efficacious in the Reduction of Symptoms and Signs of Oral Lichen Planus," 66 *J. Am. Acad. Dermatol*. 752 (2012).

Filipec et al., "The Effect of Urocanic Acid on Graft Rejection in an Experimental Model of Orthotopic Corneal Transplantation in Rabbits," 236 *Graefe's Arch. Clin. Exp. Ophthalmol*. 65 (1998).

Gruner et al., "Inhibition of Skin Allograft Rejection and Acute Graft-Versus-Host Disease by Cis-Urocanic Acid," 98 *J. Invest. Dermatol*. 459 (1992).

Matsui, "Protective Effect of cis-Urocanic Acid Eye-drops to the Ocular Inflammation Induced by the Ultraviolet Radiation," 74 *Jap. Ophthalmological Soc'y*. 36 (1970).

Matsui et al., "Protective Effect of Urocanic Acid Eye-drops to the Ocular Inflammation Induced by the Ultraviolet Radiation," 71 *Jap. Ophthalmological Soc'y*. 55 (1967).

Matsui et al., "Protective Effect of Urocanic Acid Eye-drops to the Ocular Inflammation Induced by the Ultraviolet Radiation," 71 *Jap. Ophthalmological Soc'y* 55 (1967).

Matsui, "Protective Effect of cis-Urocanic Acid Eye-drops to the Ocular Inflammation Induced by the Ultraviolet Radiation," 74 *Jap. Ophthalmological Soc'y* 36 (1970).

* cited by examiner

PHARMACEUTICAL COMPOSITION FOR INTRACELLAR ACIDIFICATION WITH CIS-UROCANIC ACID

FIELD OF THE INVENTION

This invention relates to the use of a pharmaceutically acceptable agent for acidifying cell cytoplasm and subsequently causing immunosuppression in a person or an animal, and to treatment or prevention of diseases or disorders, curable by immunosuppression.

The invention relates also to a novel pharmaceutical composition, comprising a pharmaceutically acceptable agent being able to acidify the cell cytoplasm and subsequently cause immunosuppression in the person or the animal.

BACKGROUND OF THE INVENTION

The publications and other materials used herein to illuminate the background of the invention, and in particular, cases to provide additional details respecting the practice, are incorporated by reference.

The mode of action of UV radiation in the skin is a major challenge in photoimmunology. Studies in animals and humans have established that UV exposure yields both local and systemic immunological unresponsiveness and tolerance (Schwarz 1999). The ultraviolet B (UVB) wavelengths (280-315 nm) have been found to account for most of the immunosuppressive activity of UV irradiation. The agents responsible for direct absorption of the UVB photons in epidermis include urocanic acid (UCA) and DNA. Endogenous trans-UCA, synthesized by enzymatic deamination of histidine in the stratum corneum of the skin, is directly photoisomerized to cis-UCA upon exposure to UVB radiation. It has been well demonstrated, both in vitro and in vivo, that photoisomerization of UCA plays a role in UVB-induced immunosuppression. For instance, the systemic suppression induced by UVB irradiation can be largely reversed by anti-cis-UCA antibodies in mice (Moodycliffe 1996). Furthermore, in several animal models, local or systemic administration of cis-UCA produces immunosuppressive effects similar to UVB treatment (Gruner, 1992; el-Ghorr, 1997; Garssen, 1999, Wille 1999). Some experiments have shown that UCA is capable of modulating certain functions in isolated cells of the immune system in vitro, such as antigen presentation (Beissert 1997, Holáň 1998), NK-cell cytotoxicity (Gilmour 1993, Uksila 1994), cytokine production by spleen cells (Holáň 1998), degranulation of mast cells (Wille 1999) and activation of neutrophils (Kivistö 1996).

Neither in vivo nor in vitro studies have yet clarified which immune cells actually interact with UCA after UVB exposure and by which mechanism this molecule affects the function of the target cells at the molecular level. One would expect that UCA is a soluble mediator binding to cell surface receptors and initiating a signaling cascade. However, little is known about the putative receptor(s) of UCA. It may share some common properties with the histaminergic system, because histamine $H_1$ and $H_2$ receptor antagonists partially block cis-UCA induced immunosuppression (Hart 1997). On the other hand, it has been shown that cis-UCA does not directly bind to histamine receptors (Laihia, 1998). Recently, displacement studies indicated that UCA may act on GABA receptors, but no direct evidence of UCA binding to this receptor was demonstrated either (Laihia, 1998; Uusi-Oukari, 2000).

OBJECT AND SUMMARY OF THE INVENTION

The inventors of the present invention have demonstrated a so far unknown mechanism of action of cis-urocanic acid. They have surprisingly shown that cis-urocanic acid migrates into the cell cytosol in a form which is able to release a proton in the cytosol, subsequently acidify the cytoplasm, and as a result thereof, act as an immunosuppressing agent.

Thus, according to one aspect, this invention relates to the use of a pharmaceutically acceptable agent or salt thereof being able to acidify the cell cytoplasm, for the manufacture of a pharmaceutical composition useful for causing immunosuppression in a person or an animal, wherein an effective amount of said agent is administered in an essentially non-dissociated form to the person or animal, and wherein the agent is admixed with a carrier adjusting the pH of the composition to the pH range 6.1 to 7.0.

According to another aspect, the invention concerns a pharmaceutical composition comprising as active substance a pharmaceutically acceptable agent or salt thereof being able to acidify the cell cytoplasm, in combination with a pharmaceutically acceptable carrier, which carrier essentially prevents the agent from dissociating at extracellular pH values and wherein the carrier is able to keep the pH of the composition in the range 6.1 to 7.0.

A, Cytosol of cells incubated with [$^{14}$C]cis-UCA. B, Cytosol of cells incubated with [$^{14}$C]trans-UCA. C, Elution of standard molecular weight protein markers and cis-UCA alone in the same conditions.

Figure 6:
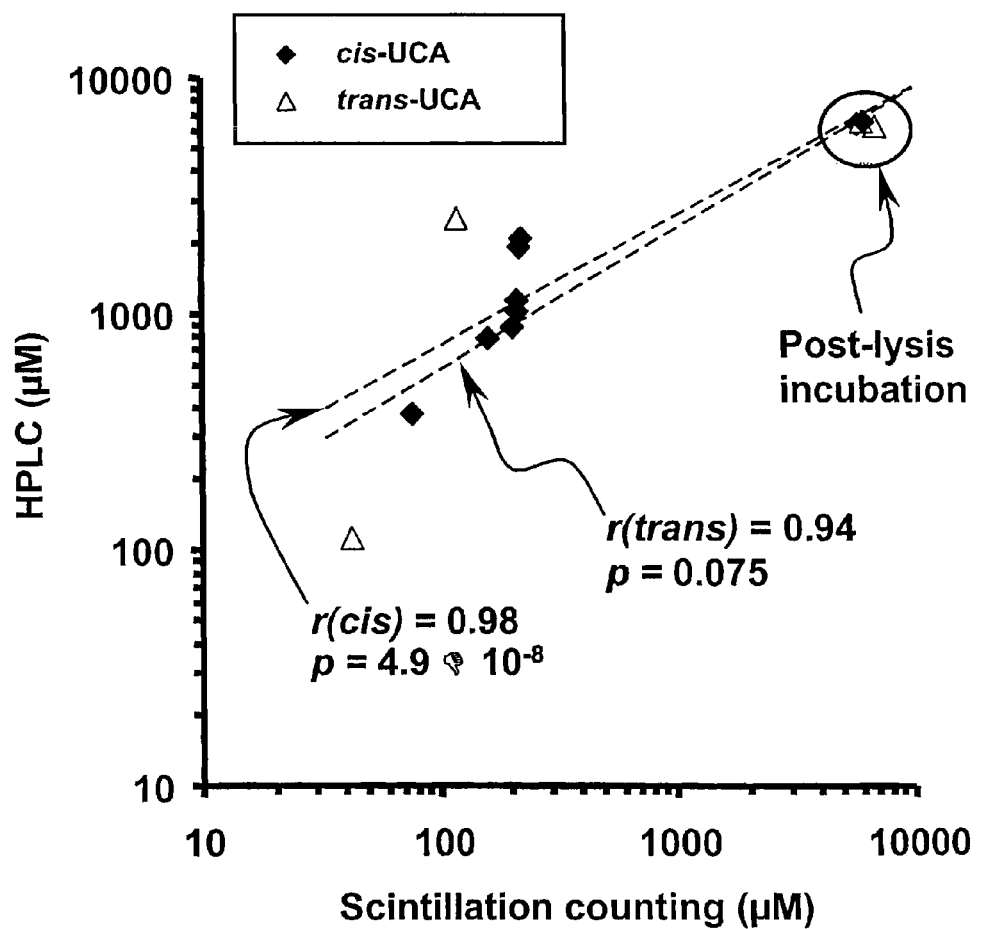

FIG. 6 shows lack of UCA metabolism in the experimental conditions. Cytosolic proteins of [$^{14}$C]UCA-labeled neutrophils from various binding assays were precipitated with 10% TCA on ice overnight. The amount of radioactive label was measured in the precipitate and protein-free supernatant by scintillation counting and the content of intact (non-metabolized) UCA isomers in the supernatant by HPLC. The data represent results from a set of whole-cell incubations with cis-UCA (n=7) and trans-UCA (n=2) and from two experiments with post-lysis incubation with both isomers (arrow). Pearson's correlation coefficients and p-values have been calculated for both isomers.

Figure 7:
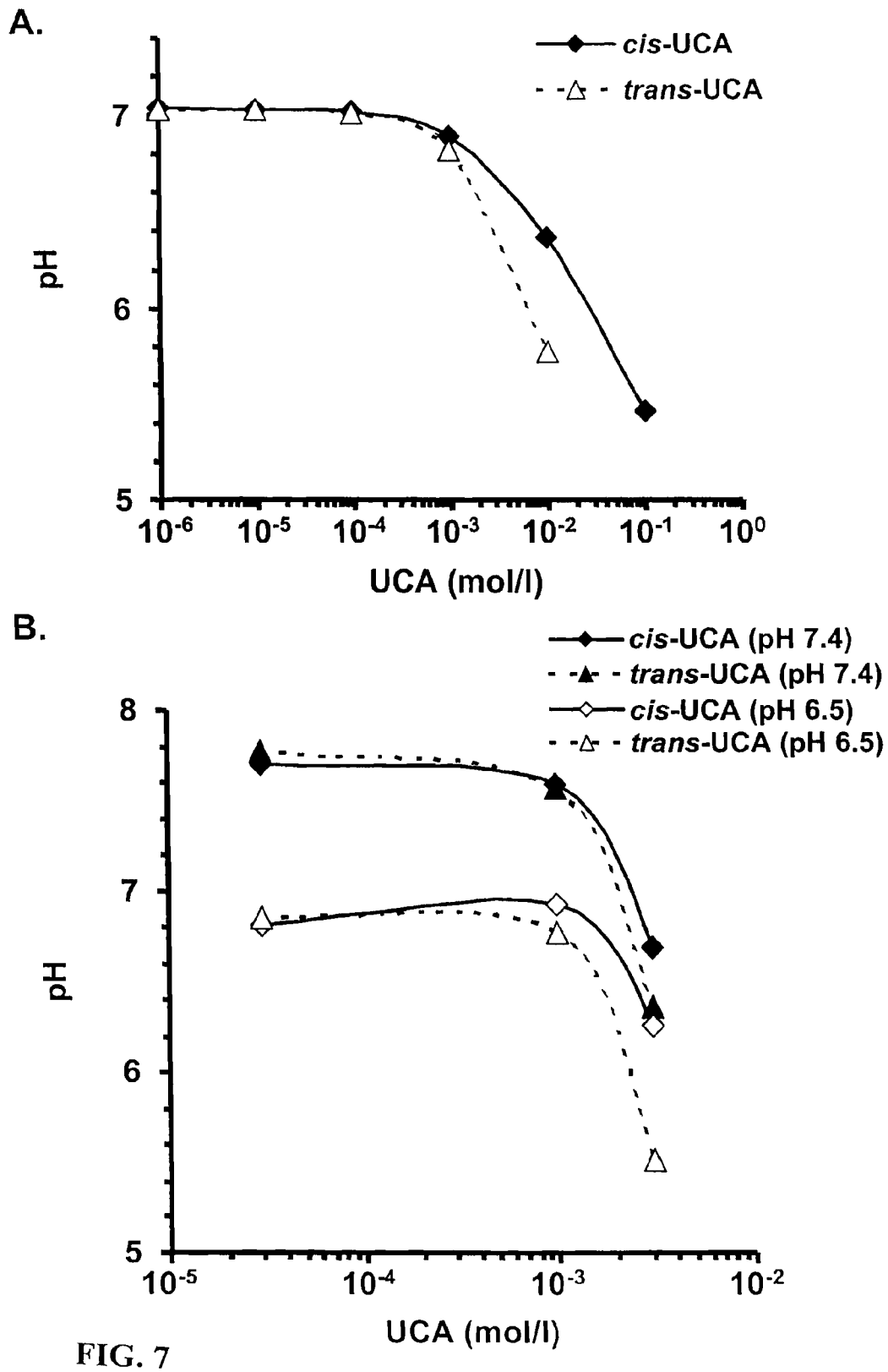

FIG. 7 shows the pH effect of UCA isomers on standard incubation buffers. The pH was measured in PBS, pH 7.0 (A), and in HBSS buffers, pH 7.4 (B), containing graded concentrations of cis-UCA and trans-UCA.

Figure 8:
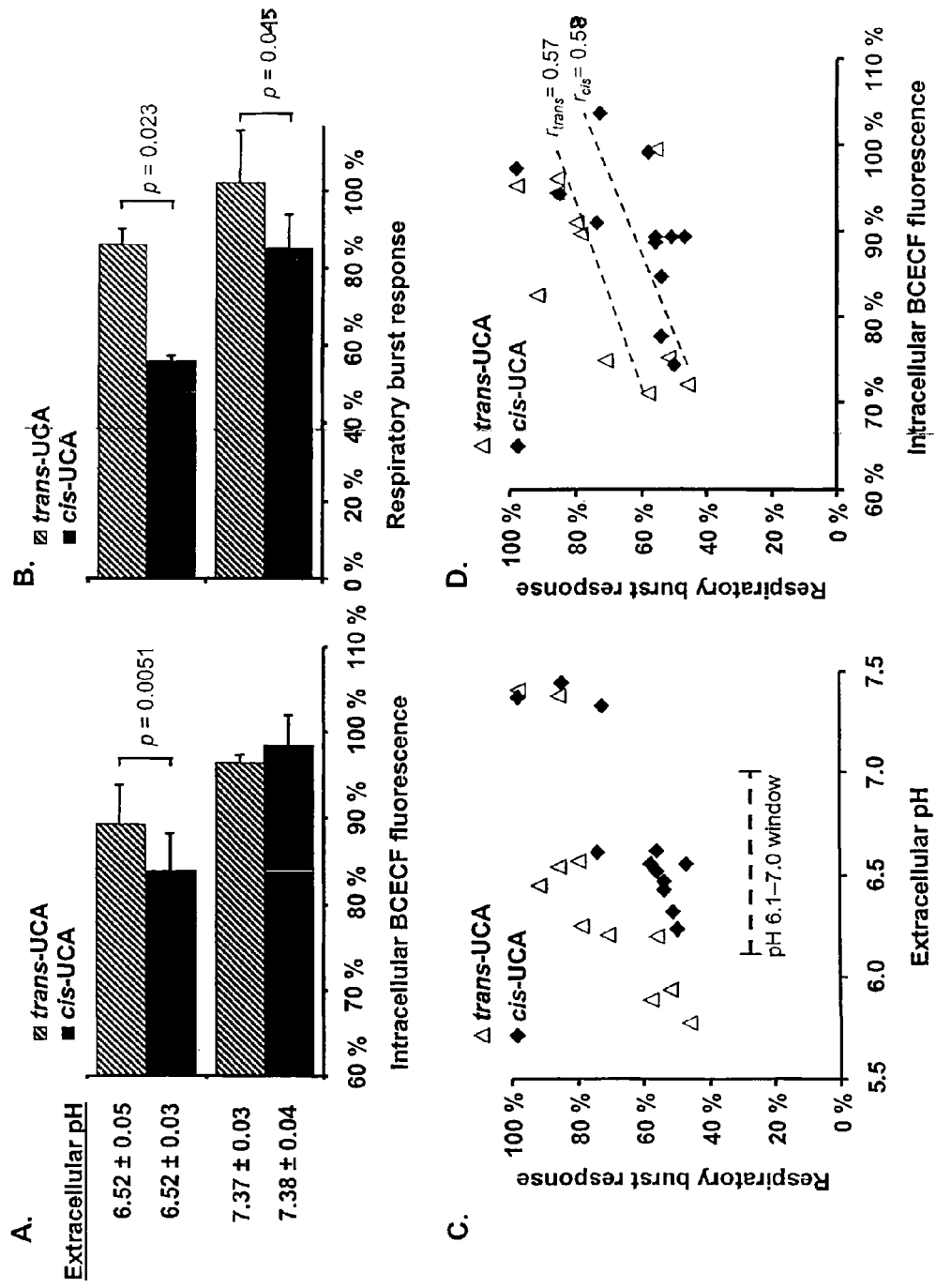

FIG. 8 shows the relation of respiratory burst activity and acidification of the cytosol by UCA isomers. In three independent experiments, neutrophils were incubated with 3 mM cis- or trans-UCA and analyzed simultaneously for respiratory burst chemiluminescence and pH indicator fluorescence. A. Intracellular pH indicator dye fluorescence compared to control levels at the same extracellular pH. The cells were loaded with BCECF, washed, incubated with UCA, and analyzed with flow cytometry. The percentages have been calculated from the geometrical mean fluorescence intensities. B. Respiratory burst responses compared to control levels without UCA at the same pH. The results are from two parallel assays within each of the three experiments. In A and B, the pH of the extracellular medium was adjusted to 6.5 or 7.4 after adding UCA. C. Respiratory burst response with UCA as a function of extracellular pH. The data are from the three experiments above complemented with simultaneous incubations where pH was measured only but not adjusted after the addition of 3 mM UCA. D. Dependence of respiratory burst on intracellular acidification. Correlation coefficients for cis- (p=0.048, n=12) and trans-UCA (p=0.065, n=11) were calculated from the same experiments as in B.

Figure 9:
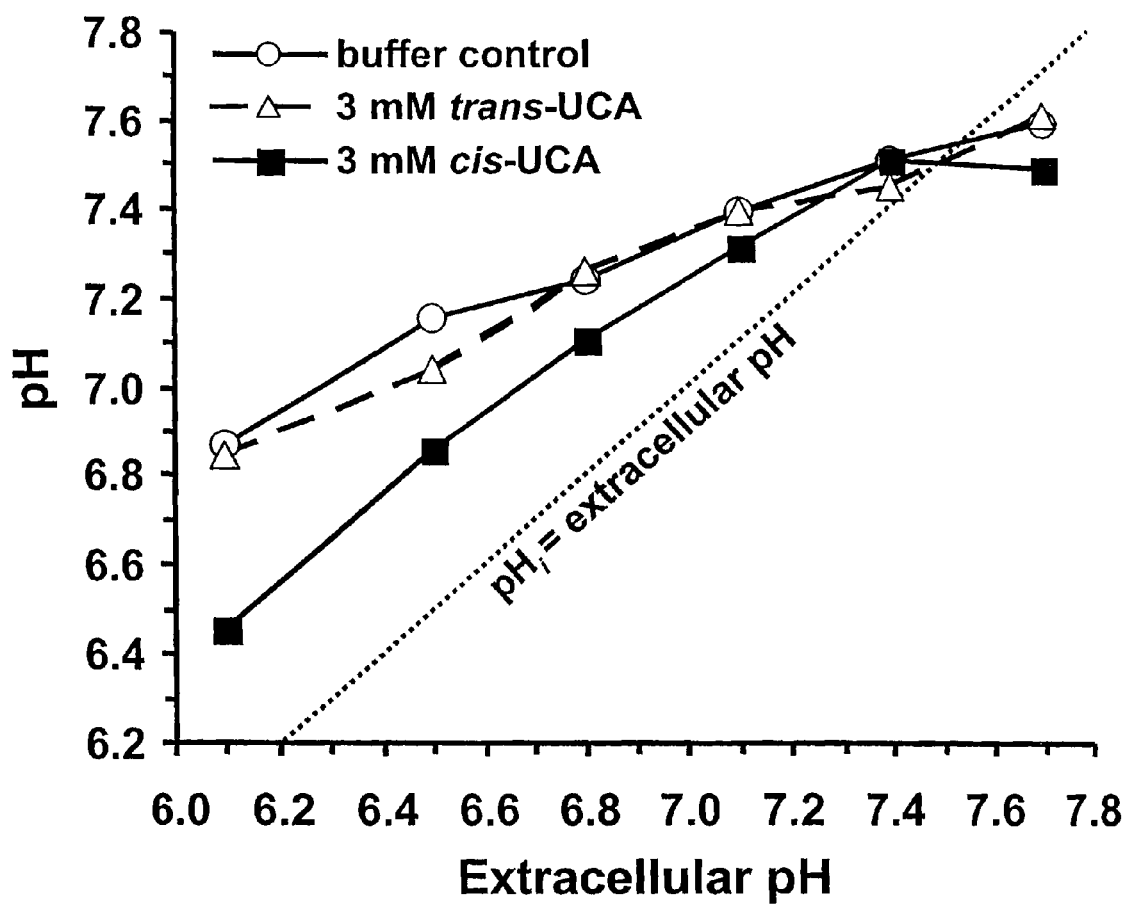

FIG. 9 shows the intracellular pH calibration in UCA-treated neutrophils in situ. BCECF-labelled cells were used as pH reference cells after treatment with proton ionophore nigericin in high-potassium Pipes buffer at various pH. Other BCECF-labelled cells were incubated with or without 3 mM UCA in low-potassium Pipes buffer adjusted to the same pH levels as those of the calibration buffers. Intracellular pH was calculated using BCECF median fluorescence intensity obtained in flow cytometry.

DETAILED DESCRIPTION OF THE INVENTION

According to a preferable embodiment, the pharmaceutically acceptable agent is an acid having its dissociation constant in the range 6.7 to 7.4, preferably in the range 6.9 to 7.3; most preferably about 7.0.

The acid is preferably cis-urocanic acid or salt thereof, but it is not restricted hereto. Any other pharmaceutically acceptable, non-toxic agent having its dissociation constant in the range defined above and being able to accumulate inside a cell would be useful. Such agents may be inorganic or organic, preferably an organic acid having, like cis-urocanic acid, a heterocyclic ring to which a saturated, or more preferably, an unsaturated carboxylic acid moiety is attached. The heterocyclic group may be, for example, an imidazole (as for cis-urocanic acid) or any other heterocyclic or poly-heterocyclic group having the ability to donate a proton at cytoplasmic pH and thereby acidify the cytoplasm. As examples of other suitable heterocyclic groups can be mentioned thiazole, thiophene, furan, oxazole, triazole, tetrazole, pyrazole, pyridine, pyrimidine and triazine.

The pharmaceutically acceptable agent is admixed with a carrier, which can be one single component, or more preferably, a mixture of two or more components. One of the components is suitably a buffering agent, which adjusts the pH of the composition to the desired value.

Especially when cis-urocanic acid is the active agent, it is preferable to adjust the pH of the composition to 6.5 to 7.0, preferably 6.7 to 7.0. In this pH range, cis-urocanic acid is still non-dissociated, while trans-urocanic acid is fully dissociated. Such a composition will therefore be specific with respect to cis-urocanic acid.

As examples of suitable buffering agents to adjust pH to 6.5-7.0 can be mentioned 50 mM sodium phosphate supplemented with 55 mM sodium chloride, 50 mM sodium citrate supplemented with 120 mM sodium chloride, and 10 mM Pipes supplemented with 133 mM sodium chloride.

The method and composition according to this invention is useful for treatment or prevention of any disease or disorder curable by increased immunosuppression. The term immunosuppression used herein refers to regulation, typically down-regulation, of the body's immune system by affecting to the activity and function of the cells of the immune system in a way which prevents the undesired adverse effects of an immune response. Examples of the target cells of the method and compositions of the present invention are granulocytes (neutrophils, eosinophils, basophils), NK-cells, T- and B-lymphocytes, monocytes, macrophages, mast-cells and antigen presenting cells, such as dendritic cells, and their precursor cells and specific functional and phenotypic subsets. Most preferably the target cells of the method and compositions of the present invention are cells of the innate immune system, such as neutrophils and NK-cells.

It is well established that the appropriate function of cells of the immune system is vital for host's survival against invading pathogens, parasites and even physical hazards (e.g. microscopic particles inhaled) found in the living environment. Normally, immune cells recognize, isolate and eliminate locally infectious/damaging agents in a well-orchestrated process. For this purpose, the immune cells are armed with various biochemical response mechanisms, which become active during the infectious attack. For example, neutrophilic leukocytes, neutrophils, contain a highly specific enzyme complex, NADPH oxidase system, which, when triggered upon cell activation, is able to generate large amount of toxic oxygen metabolites, which can exert a number of damaging effects against biological material, and may also act as proinflammatory signals for other cells types. In general, leukocyte activation leads to a local inflammatory reaction which is an essential part of host's immune response and which promotes the resolution of the infectious assault and initiates the healing process. However, if normal host tissues are inappropriately identified as foreign or damaged structures, or due to the hyperactivation of host's immune system associated with some pathological states, normal tissue is attacked by immune cells which elicit their full destructive potential against host itself. As examples of such states can be mentioned groups of conditions such as local and systemic inflammatory diseases, autoimmune diseases and allergic conditions. As examples of specific diseases or disorders can be mentioned hypersensitivity reactions such as contact hypersensitivity or delayed type hypersensitivity. Preferably the condition which can be treated or prevented by the method and compositions of this invention is a local or systemic inflammatory reaction which involves the activation of the preferable target cells, such as inflammatory conditions of the skin, including psoriasis, acute or chronic dermatitis; inflammatory conditions of mucous membranes or the connective tissue of the oral cavity, eyes and genitals, such as periodontitis, conjunctivitis, vaginitis; inflammatory conditions of mammary glands, including mastitis; or any other local or systemic condition manifesting a recognized inflammatory component in the disease pathogenesis or progression, such as vasculitis, acute graft rejection, chronic obstructive pulmonary disease, asthma, reperfusion injury, and sepsis associated tissue damage. However, the conditions that can be treated or prevented according to this invention are not restricted to the aforementioned examples.

For the purpose of this invention, the pharmaceutically acceptable agent can be administered by various routes, either systemically or locally. The suitable administration forms include, for example, oral formulations; parenteral injections including intravenous, intramuscular, intradermal and subcutaneous injections; and mucosal, topical, transdermal, inhalation, nasal or rectal formulations. Particularly suitable formulations are formulations for local delivery such as topical formulations in the form of ointments, gels, creams, pastes, solutions, suspensions, lotions and emulsions.

The required dosage of the pharmaceutically acceptable agent will vary with the particular condition being treated, the severity of the condition, the duration of the treatment, the administration route and the specific compound being employed. In a topical formulation the amount of the pharmaceutically acceptable acid can typically range from 0.01% to 50%, preferably in the range 0.1 to 10%.

The invention will be illuminated in detail in the following Experimental Section.

EXPERIMENTAL SECTION

The aim of the present study was to investigate the binding of radiolabeled UCA in a model cell, the human peripheral blood neutrophil, which has been show to be affected by UCA (Kivistö 1996). Instead of being able to demonstrate a typical ligand-receptor interaction, we found that UCA has an exceptional binding property, which leads to rapid and irreversible accumulation of intact UCA into the cytosol. Urocanic acid is an UV radiation-absorbing substance in the mammalian skin. The cis-UCA is an immunosuppressant in animal models in vivo, but the target cell type(s) and mode(s) of action have remained obscure. We investigated the binding and the site of action of UCA in live human polymorphonuclear neutrophils, an immune cell type whose function is known to be affected by UCA and which is known to play a major role in inflammatory reactions. We observed a linearly concentration-dependent accumulation of radiolabeled cis- and trans-UCA up to unexpectedly high incubation concentrations ($\geq$30 mM) with almost 95% of the cell-bound fraction concentrating in the cytosol. Because the isomers appeared in an unbound and non-metabolized form in the cytosol, we questioned whether UCA could act through a mechanism different from conventional receptor/protein-ligand interaction. The isomers affected intracellular pH. FACS analyses showed that acidification of the intracellular compartments of neutrophils by cis-UCA at extracellular pH 6.5 was significantly greater than by trans-UCA ($p=0.00031$), whereas the isomers did not acidify at pH above neutral. In the same conditions at pH 6.5, cis-UCA inhibited the respiratory burst activity of neutrophils more than trans-UCA ($p=0.023$). Stereospecificity of this type could be explained by dissimilar $pK_a$ values of the two isomers, and we propose a model for cis-UCA action through intracellular acidification. We conclude that cis-UCA may suppress innate immunity by inhibiting neutrophil activation and function through intracellular acidification in an extracellular pH 6.1-7.0 window.

Methods

Urocanic Acid and Synthesis of [$^{14}$C]-Labeled Isomers

Trans-urocanic acid (trans-UCA, 3-(1H-imidazol-4-yl)-2-propenoic acid) was purchased from Sigma (St. Louis, Mo., USA). Cis-UCA was prepared from trans-UCA with UV photoisomerization (see below). The chemical purity of the UCA isomers was above 99.7% by high-pressure liquid chromatography (HPLC).

Figure 1:
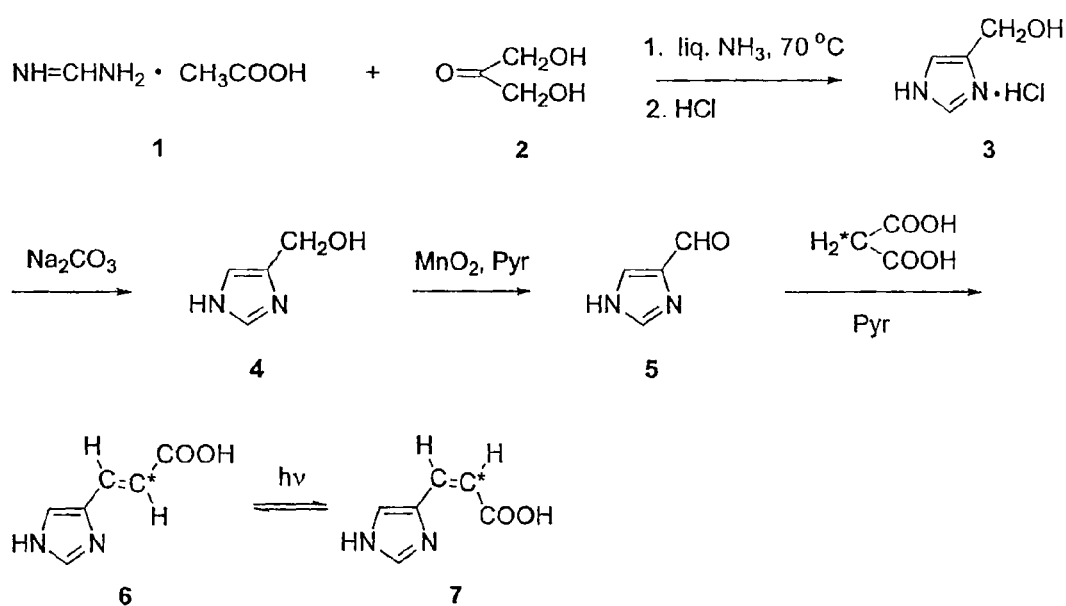
FIG. 1 is a scheme for the chemical synthesis of $[^{14}C]$-radiolabeled trans- and cis-UCA.

The synthesis of [$^{14}$C]-radiolabeled trans- and cis-UCA is outlined in FIG. 1. We started the synthesis of [$^{14}$C]trans-UCA (6) by condensing formamidine acetate (1) and dihydroxyacetone (2) in liquid ammonia to give (3), utilizing the procedure of Griffith et al. (1983) with several modifications. After neutralization of (3) to the free base (4), it was oxidized to 4-imidazolecarbaldehyde (5) (Lindgren et al., 1980). Condensation of (5) with [2-$^{14}$C]malonic acid (Amersham Pharmacia, Little Chalfont, UK) under Knoevenagel conditions using a modified method of Morrison et al. (Mohammad 1991) afforded trans-UCA (6). Compound (6) (138 mg, 1 mmol) was dissolved in water (500 ml). The solution was brought to pH 9 with solid potassium hydroxide and then irradiated under nitrogen atmosphere at 10° C. for 4 h. Photoisomerization was performed in a Normag falling-film photoreactor with Hanau quartz mercury high-pressure lamp (500 W, 270-350 nm, water as solvent). The resulting mixture (trans/cis ca. 30/70 by HPLC) was evaporated to dryness and the residue dissolved in 12.5 mM acetic acid. This solution was adjusted to pH 9 and chromatographed on an ion exchange column (25×2.3 cm, 200-400 mesh, acetate form, Bio-Rad 1-×8) using 12.5 mM (500 ml), 25 mM (500 ml), and 100 mM (1000 ml) acetic acid as successive eluents. Cis-UCA appeared after ca. 1100 ml and trans-UCA mainly after 1300 ml eluent volumes. Removal of the solvent from the fractions, followed by washing with diethyl ether and drying in vacuo at 65° C. over phosphorus pentoxide, yielded the pure [$^{14}$C]trans- and [$^{14}$C]cis-isomers (6) and (7). The yield of (6) from the preceding step was 35 mg (25%), mp. 226° C. The chemical purity of the product (6) by HPLC (see below) was above 99.8%, and the specific activity was 2.2 mCi/mmol. The corresponding yield of (7) was 85 mg (58%), mp. 176-178° C. HPLC analysis indicated the material to be more than 99.5% chemically pure with a specific activity of 5.8 mCi/mmol. When used in the experiments, the radiolabeled and non-labeled cis- and trans-isomers were dissolved directly in the incubation buffers up to 100 mM and 30 mM concentrations, respectively. The dissolution of trans-UCA was aided with gentle warming in a water bath when needed.

HPLC Analysis of UCA

An aminopropyl stationary phase column Lichrosorb NH$_2$, Hibar RT, 250×4 mm, 5 µM (Merck, Darmstadt, Germany) was used. The eluent was a 50% (v/v) mixture of acetonitrile and a solution of 2% (v/v) acetic acid and 0.5% (w/v) ammonium acetate in water (pH ca. 5). The isomers were detected at 268 nm, and the retention times were $T_r$(cis) 3.7 min and $T_r$(trans) 5.4 min.

Scintillation Counting

Samples were mixed with OptiPhase HiSafe 2 scintillation liquid (EG&G Wallac, Turku, Finland) and [$^{14}$C]UCA radioactivity measured in RackBeta 1214 scintillation counter (EG&G Wallac). The counting efficiency was 96.7%±0.12% (mean±SEM, n=48).

Purification of Neutrophils

Peripheral blood neutrophils were isolated from heparinized blood or buffy coats of healthy donors. Erythrocytes were sedimented with 6% dextran T-500 (Pharmacia, Sweden). Neutrophils were separated from the leukocyte-rich dextran plasma by centrifugation on Ficoll-Hypaque (Pharmacia), purified by hypotonic lysis of remaining erythrocytes, and washed with Ca- and Mg-free HBSS. For the intracellular pH experiments, neutrophils were prepared without erythrocyte lysis. The cells, media and centrifuges were kept at room temperature during cell preparation to avoid temperature fluctuations. By flow cytometry analysis, 99.6% of the separated neutrophils were $CD11b^+/CD35^+$, 98% $CD45^+$, 98% $CD62L^+/CD32^+$, 2.0% $HLA-DR^+$, 2.1% $CD3^+$, 1.0% $CD8^+$, 1.2% $CD4^+$, and 0.8% $CD14^+$ cells.

Assay for Respiratory Burst Activity

The respiratory burst activity was used as a measure of neutrophil function. The UCA isomers were tested in a chemiluminescence assay with opsonized zymosan as described (Kivistö et al. 1996). The peak values were recorded.

Whole-Cell Binding Assays

Isolated neutrophils were resuspended in HBSS, pH 7.4, at $2-10\times10^6$ cells/ml. The [$^{14}$C]cis- or [$^{14}$C]trans-UCA stock solutions were added to yield a concentration range 0.1 µM-30 mM, and the tubes, in duplicate, were incubated at 4° C. (or at 25° C. and 37° C.) for 30 min. The cells were then washed once with ice-cold HBSS and transferred into liquid scintillation vials. The total [$^{14}$C]UCA activity in the incubation tubes was determined by measuring samples from each standard concentration, and blank scintillation values were subtracted before data analysis. Some binding experiments were performed in 50 mM sodium citrate/120 mM NaCl buffer, pH 6.5, as indicated, using the same buffer in washing steps.

Preparation of Neutrophil Cytosol and Membrane Fractions

The localization of the cell-bound UCA in membrane, cytosol and nucleus was investigated after the incubation of whole cells with [$^{14}$C]cis-UCA as described above. After washing with HBSS, the cells were suspended ($200\times10^6$ cells/ml) in ice-cold lysis buffer containing 10 mM Pipes, 10 mM KCl, 3 mM NaCl, 4 mM $MgCl_2$, pH 7.0, supplemented with 0.5 mM PMSF, 10 µM leupeptin, and 10 µM pepstatin A (all from Sigma) as proteinase inhibitors. The cell membranes were broken by sonication on ice. The lysate was centrifuged (800×g, 25° C., 10 min), and the post-nuclear supernatant was layered on discontinuous cushions of sucrose in lysis buffer. After ultracentrifugation (120 000×g, 4° C., 45 min), the cytosol, membrane, and nuclei/debris fractions were recovered by careful pipetting, and [$^{14}$C] activity was measured.

Gel Filtration of Neutrophil Cytosol

For the macrofractionation of cytosol proteins, the sample (0.5-2.5 ml) was applied to the balanced Sephacryl S-200 gel filtration (Pharmacia) column at 4° C., and the proteins were eluted with PBS, pH 7.0, at a flow rate of about 0.6 ml/min. The elution of proteins was followed with a flow-through UV monitor at 254 nm and a potentiometric recorder. A typical run consisted of thirty 6-ml fractions and lasted for almost six hours. The elution volumes of proteins of different molecular weights were determined with a cocktail of standard proteins and peptides of 0.6-2000 kDa size.

Protein Concentration Assay

Protein concentration was determined with Bio-Rad (Munich, Germany) protein assay using bovine albumin as a standard.

Monitoring of Intracellular pH

Intracellular pH levels in neutrophils were monitored with flow cytometry utilizing a pH-sensitive fluorescent dye 2',7'-bis-(2-carboxyethyl)-5-(and -6)-carboxyfluorescein (BCECF, acetoxymethyl ester; Molecular Probes, Leiden, The Netherlands). About $30\times10^6$ cells were incubated in 10 ml HBSS, pH 7.4, containing 0.35 µM BCECF at 25° C. for 30 min, washed twice in HBSS, and resuspended in 1 ml of 154 mM NaCl. Aliquot (235 µl) of the incubation medium with known UCA concentrations and checked pH was applied to the cells ($4.5\times10^5$ cells/15 µl NaCl) in polystyrene tubes, incubated at 25° C. for about 20 min, and analyzed in a flow cytometer.

Calibration of intracellular pH was performed in situ using the $K^+/H^+$ ionophore nigericin. An excess of pH calibration buffers (10 mM Pipes, 131 mM KCl, pH adjusted to 6.10, 6.50, 6.80, 7.10, 7.40, and 7.60. or 7.70) and 10 µM nigericin was added to the BCECF-labelled cells in 154 mM NaCl. The cells were kept at room temperature and analysed by flow cytometry within 45 min. Cells incubated with or without UCA were analysed for intracellular pH simultaneously. The pH was adjusted to the same values as those in the calibration buffers. Intracellular pH was determined from a BCECF fluorescence intensity calibration curve.

Statistical Analysis

The results have been presented as mean SEM. Statistical significance of data in the binding studies and functional tests were calculated with two-way Student's t test. The Pearson's correlation coefficients were determined for UCA isomer concentrations detected by HPLC and scintillation counting of cell samples. The p-values for correlation were determined after Fisher's Z transformation.

Results

UCA Accumulates in Neutrophil Cytosol

Figure 2:
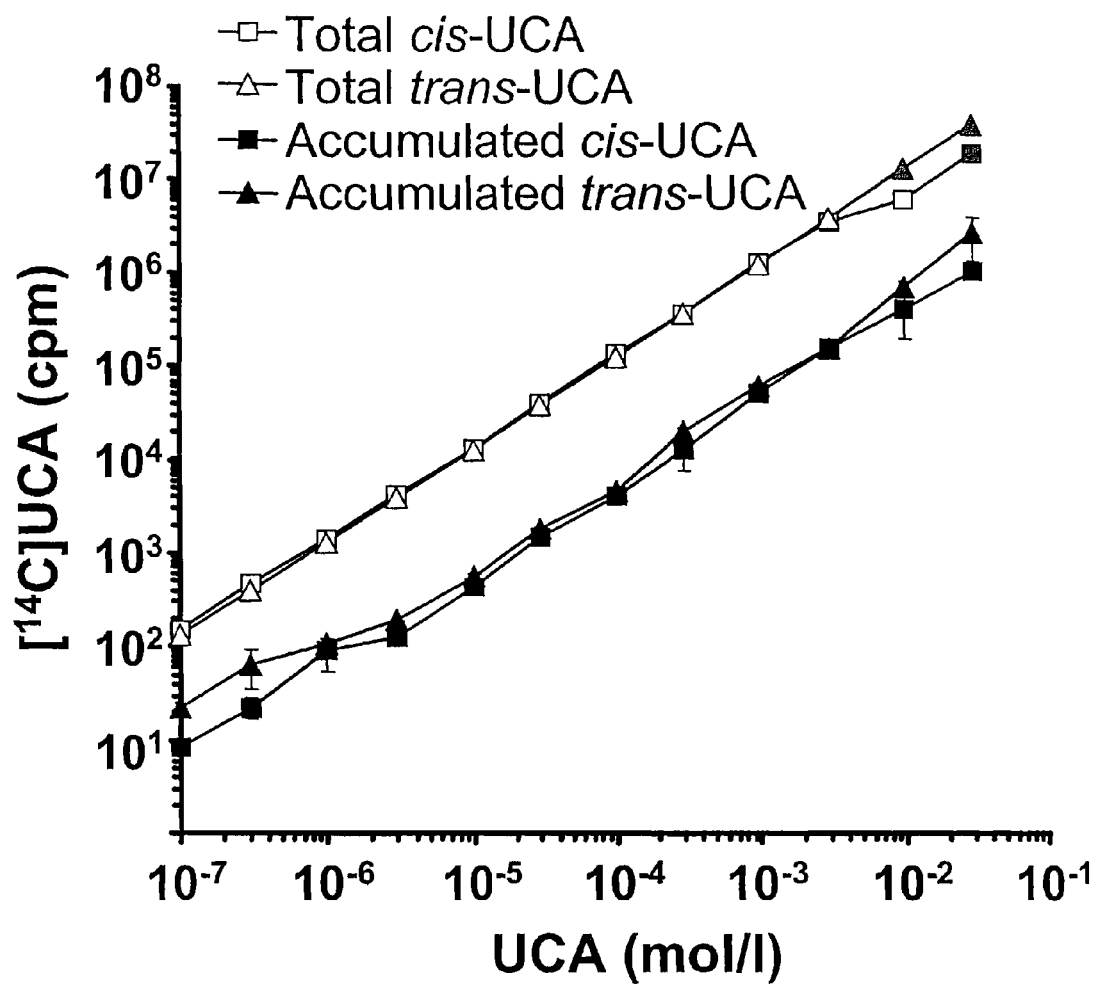
FIG. 2 shows accumulation of UCA to live neutrophils. The data points represent the mean±SEM in duplicate tubes after subtracting the blank value. The cells ($7.0 \times 10^6$ cells/ml HBSS) were incubated with the $[^{14}C]$UCA isomers at 4° C. for 30 min, washed, and transferred into scintillation vials. Control vials without cells, designated as "total UCA", underwent a similar incubation to eliminate any non-specific binding effect by the incubation tubes. Hatched symbols, Estimated cpm values have been used for total UCA samples with $>10^7$ cpm due to technical maximum count limit.
Figure 3:
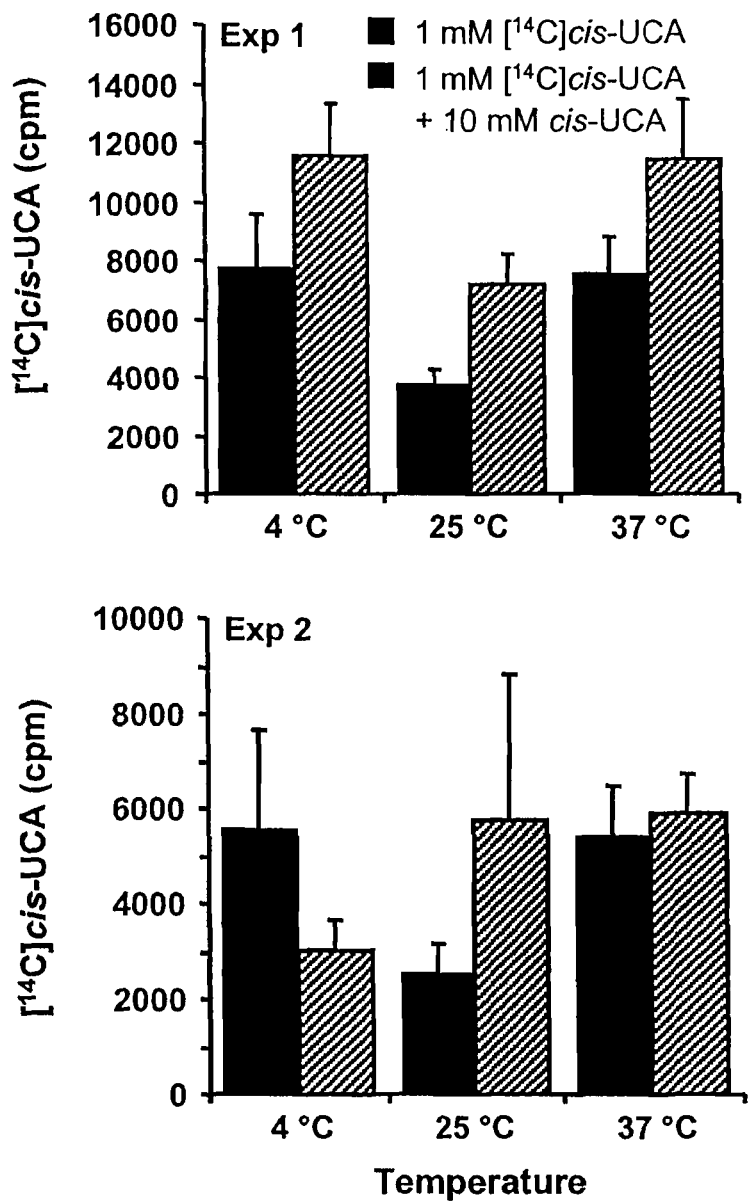
FIG. 3 shows displacement of $[^{14}C]$cis-UCA incorporation by non-labeled cis-UCA. Neutrophils isolated from freshly drawn venous blood of a single volunteer were assayed at two occasions (seven days apart) for displacement at pH 7.4. The cells ($7.4 \times 10^6$/ml in Exp 1 and $6.3 \times 10^6$/ml in Exp 2) were incubated in HBSS containing 1 mM $[^{14}C]$cis-UCA with or without 10 mM non-labeled cis-UCA (total volume 200 µl) at the indicated temperatures for 1 h. In Exp 1, the cells were washed after incubation as a pellet only, whereas the cells were resuspended in washing medium (HESS) in Exp 2. The data are from triplicate incubations.

Radioactive, [$^{14}$C]-labeled UCA isomers were synthesized to examine the binding of UCA to isolated human peripheral blood neutrophils. The cells, incubated with UCA in HBSS at 4° C. for 30 min, incorporated both isomers in a linear dose-dependent manner over the studied concentration range of 100 nM to 30 mM (FIG. 2). The proportion of total binding was 4.5%±1.1% (range 2.9-6.6%) for cis-UCA and 7.1%±3.2% (range 3.7-17%) for trans-UCA (n=12 measurements in duplicate for both isomers). An interesting feature of this uptake was that we were unable to demonstrate displacement of the [$^{14}$C]UCA radiolabel with non-labeled ("cold") UCA as one would expect in conventional ligand-receptor binding (FIG. 3).

Figure 4:
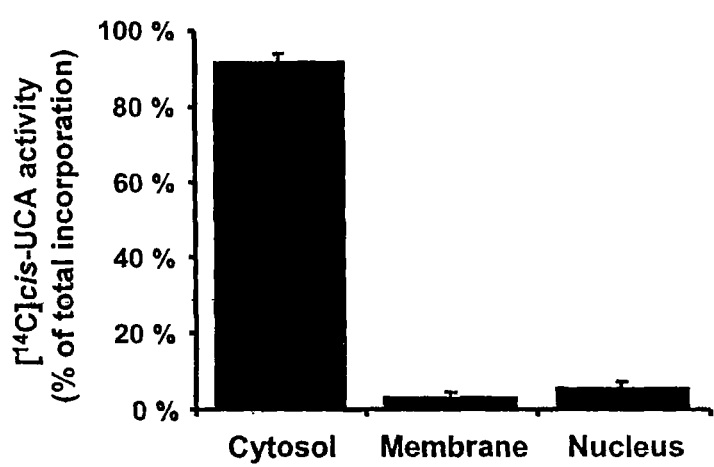
FIG. 4 shows the distribution of incorporated cis-UCA in cellular fractions and by incubation temperature. A, Proportional $[^{14}C]$ activity in different fractions of cells incubated at 4° C. (mean±SEM, n=4 independent experiments). Neutrophils ($50\text{-}200 \times 10^6$ cells/ml) isolated from buffy coats were incubated with 1 or 5 mM $[^{14}C]$cis-UCA at 4° C. for 20-30 min. The cells were disrupted by sonication, the cellular fractions were separated by sucrose ultracentrifugation, and the bound activity was measured in each fraction. B, Effect of incubation temperature on the uptake of cis-UCA to neutrophils of the peripheral blood (mean±SEM, n=4 independent experiments). C, Distribution of cis-UCA in cellular fractions according to incubation temperature (mean±SEM of duplicate incubations).

To investigate the distribution of the cell-bound UCA in the cytosol, cell membrane, and nuclear compartments, the cells were first incubated with radiolabeled UCA as above, and then they were lysed and fractionated on 120.000×g sucrose cushions. The contents in the ultracentrifuge tubes were divided into cytosolic, membrane and nuclear fractions. The volume of each fraction was determined accurately. Then the [$^{14}$C]UCA activity in aliquots of the fractions was measured, and the total UCA content was calculated for each fraction. Independent incubation experiments (n=4) showed that 92.0%±2.2% of the neutrophil-incorporated cis-UCA was recovered in the cytosol (FIG. 4A). Binding to membranes (mean 2.7%±1.8%) was significantly lower than what was found in the cytosol ($p=3.7\times10^{-5}$). The remaining cell-bound cis-UCA (5.3%±2.1%) was detected in the nuclear (and possibly non-lysed cell) fraction of the cell lysate (FIG. 4A).

UCA is not Bound to Cytosolic Proteins

Figure 5:
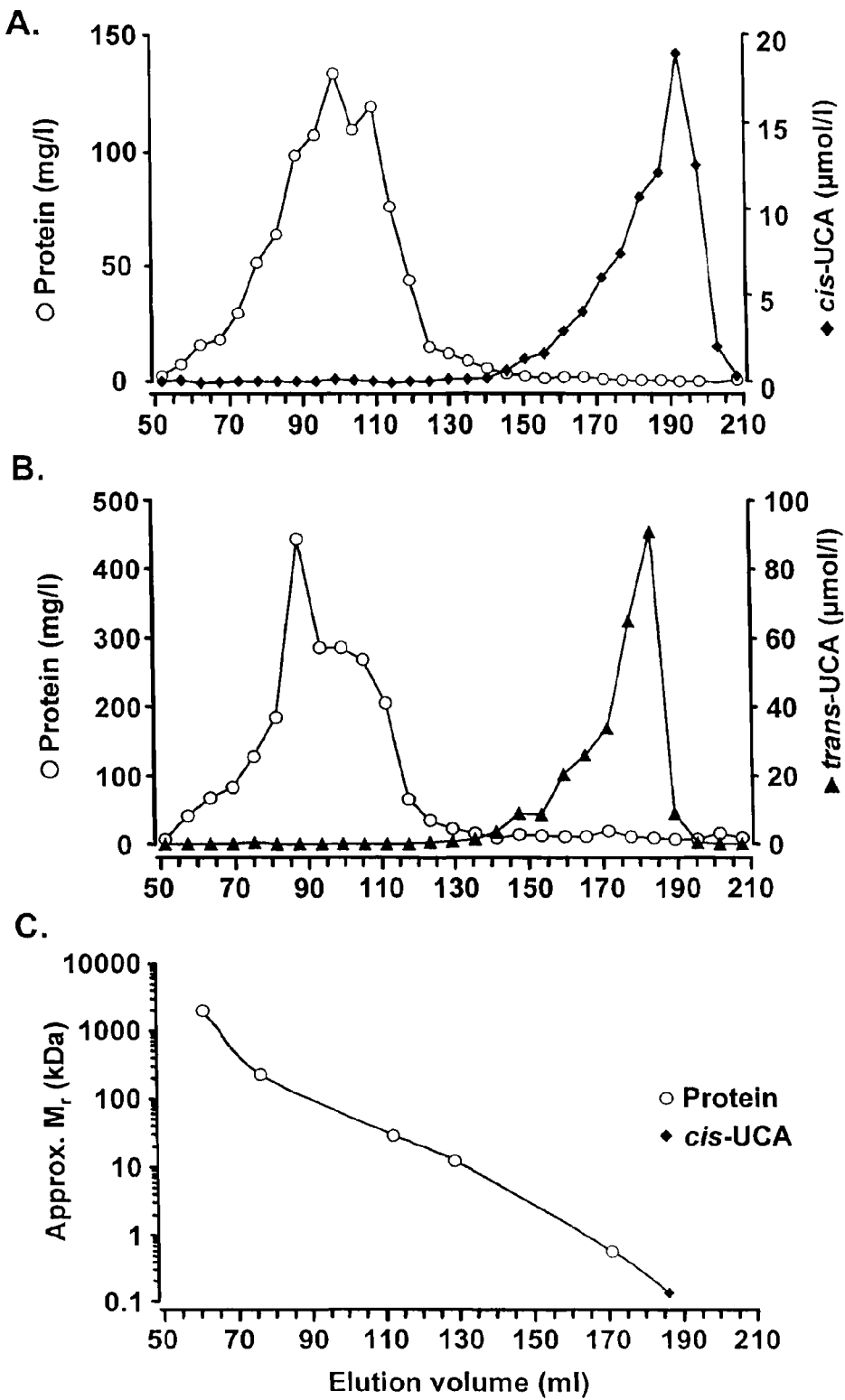
FIG. 5 shows the elution of cytosol-associated $[^{14}C]$UCA in S-200 gel filtration. Neutrophils ($160\text{-}190 \times 10^6$) were incubated with 1 mM $[^{14}C]$UCA isomers at 4° C. for 20 min, washed, lysed, and fractionated with sucrose ultracentrifugation. The cytosolic fraction was applied to the gel, and the protein content and UCA activity were measured in the elute.

As most of the UCA that incorporated in the cells appeared in the cytosol, we determined if the cytosolic UCA was bound to molecular components of the neutrophil cytosol. Cytosol of [$^{14}$C]UCA-preincubated cells was separated with sucrose ultracentrifugation and applied into S-200 gel filtration column. Cytosol fractions were then collected and the radioactivity was measured in each fraction. As shown in FIGS. 5A and 5B, [$^{14}$C] activity was found in low-molecular-weight fractions containing no detectable protein. This elution pattern was identical to a run where [$^{14}$C]cis-UCA alone was applied into the gel filtration column (FIG. 5C), suggesting that UCA is not bound to any major soluble protein fraction in neutrophil cytosol.

An additional, post-lysis labeling test was carried out to verify the results from the experiments with [$^{14}$C]UCA-preincubated cells. In this test, non-labeled neutrophil cytosol was separated as described and aliquots of the cytosol were then incubated with 5 mM cis- or trans-[$^{14}$C]UCA overnight on ice. The cytosol was then fractionated on S-200. No protein-associated [$^{14}$C]UCA activity was observed, and elution profiles similar to pre-lysis incubation were recorded. Thus, the main soluble protein fractions in the neutrophil cytosol were shown to be incapable of binding accumulated UCA before and after cell lysis.

UCA Remains Intact in Neutrophil Cytosol

Next, we examined whether the [$^{14}$C]UCA in the cytosol was metabolized by neutrophils after the uptake by determining how much of the radioactive label was associated with intact UCA. This was carried out by precipitating the cytosolic proteins of [$^{14}$C]UCA-labeled neutrophils with 10% trichloracetic acid (TCA) on ice overnight. The amount of radioactive label was then measured both in the precipitate and in the protein-free supernatant by scintillation counting, and the content of intact UCA in the supernatant by HPLC. All [$^{14}$C]UCA activity was found in the supernatant, the recovery being 102%±3.9% (n=9) for cis-UCA and 100.2%±0.9% (n=4) for trans-UCA when the radioactivity in the cytosol immediately after the addition of TCA and after spinning down the protein precipitate was compared. No radioactivity was found in the protein pellet. More importantly, the chromatographically determined concentrations of intact cis- and trans-UCA correlated with concentrations achieved by scintillation counting in the same samples (FIG. 6), indicating that UCA isomers were not metabolized in neutrophil cytosol. No endogenous UCA could be found by HPLC analysis in cells that were not pretreated with UCA isomers (data not shown).

UCA Lowers Extracellular and Intracellular pH

The results reported so far show that instead of behaving like a typical cell-surface receptor agonist, UCA accumulates in high concentrations inside a neutrophil, where it is not bound to soluble intracellular proteins nor subject to significant metabolism. As such, UCA resembles small ions (e.g., $K^+$, $Na^+$, $H^+$, $Cl^-$) which enter the cell and modulate cell functions by altering the physico-chemical micro-environment (pH, ion potential, ion strength) of the cytosol. Therefore, we hypothesized that the high levels of intact UCA may provoke cellular changes simply due to its passive presence in the cytosol as an acid. The $pK_a$'s being around 4.0 and 6.1 for trans-UCA (Roberts et al. 1982, Krien & Kermici 2000) and 3.3 and 7.0 for cis-UCA (Roberts et al. 1982), one possible mode of action could be the acidification of the cytosol at physiological pH. Such a possibility was approached by testing the effect of UCA on pH first in a buffer solution and then in intact cells. The isomers lowered the pH in a standard PBS buffer, pH 7.0, in a dose-dependent manner at concentrations above 1 mM (FIG. 7A). When UCA isomers were added in HBSS buffer, pH 7.4, concentrations above 1 mM again dropped the pH dose-dependently (FIG. 7B). Interestingly, when the pH of HBSS buffer solution was adjusted to 6.5 prior to UCA addition, i.e. below the second $pK_a$ of cis-UCA, only trans-UCA was able to markedly reduce the pH (FIG. 7B), suggesting that cis-UCA is only partly deprotonated at this pH.

To test the effect of UCA on intracellular pH, neutrophils were loaded with the fluorescent pH-indicator dye BCECF, and the fluorescence of UCA-treated cells was measured with FACS. As the data above indicate, UCA itself can lower the pH of the test solution depending on isomer and initial pH of the solution. On the other hand, it is well known that the intracellular pH is affected by the pH of the environment. Therefore, in order to avoid the artefact that the acidification of the test solution by UCA addition might affect intracellular BCECF fluorescence, we adjusted the pH of the test solution back to the original pH after the addition of UCA. In these pH-controlled conditions, 3 mM trans- and cis-UCA had no significant effect on the intracellular BCECF signal at pH 7.4 (FIG. 8A, lower bars). In contrast, when the pH was adjusted to 6.5, cis-UCA caused a significant reduction by 15%±4.0% (p=0.022, n=4, paired t test) in the fluorescence signal as an indication of cytosolic acidification (FIG. 8A, upper bars). FIG. 8 shows data from three independent experiments measuring simultaneously BCECF signals and respiratory burst activity of the cells (see below). A fourth experiment was performed for intracellular BCECF fluorescence measurement only. Also trans-UCA decreased the fluorescence signal significantly by 9.4%±4.1% at pH 6.5 (p=0.032, n=4), but the effect was less pronounced. However, the difference in proportional BCECF fluorescence reduction between 3 mM cis-UCA and trans-UCA was highly significant (p=0.00031, n=4) (FIG. 8A, upper bars).

To achieve a more specific view of the ability of cis-UCA to acidify the cytosol, the exact intracellular pH was determined by the use of the $K^+/H^+$ ionophore nigericin. Incubation of neutrophils with UCA in buffered solutions of several pHs in the range 6.1-7.7 demonstrated that 3 mM cis-UCA lowers the intracellular pH in dose- and extracellular pH-dependent manner below pH 7, whereas trans-UCA has only a minor effect (FIG. 9). The 0.3 mM concentration of cis-UCA had a much smaller effect in the same pH range (not shown).

UCA Inhibits Neutrophil Respiratory Burst Stereospecifically and pH-Dependently

The data shown above suggest that in a slightly acidic environment only cis-UCA is able to markedly decrease cytosolic pH whereas at physiological pH neither trans-nor cis-isomer had any effect. To examine how the cytosol-acidifying effect of UCA correlates with the previously reported inhibition of neutrophil respiratory burst activity, we measured the effect of 3 mM UCA on opsonized zymosan-induced chemiluminescence by the same batch of neutrophils and in the same experimental conditions described above, i.e. when the pH of the test solution was adjusted back to its initial level after UCA addition. As shown in FIG. 8B, trans-UCA had no effect on chemiluminescence at pH 7.4, whereas an inhibition of 14%±4.0% (n=3) was observed at pH 6.5. In the same conditions, cis-UCA suppressed the respiratory burst activity by 15%±8.4% and 44%±1.3%, respectively. Interestingly, when the pH of the test solution was left unadjusted after UCA supplementation, trans-UCA inhibited the chemiluminescence by 31%±8.4% and 48%±4.0% at pH 6.22±0.02 (nominal pH 7.4) and 5.87±0.06 (nominal pH 6.5), respectively. The corresponding inhibitions for cis-UCA were 41%±10% at pH 6.60±0.02 (nominal pH 7.4) and 48%±1.6% at pH 6.33±0.07 (nominal pH 6.5).

When the obtained respiratory burst response data is plotted against the measured pH in the incubation medium, it is evident that lowering the extracellular pH suppresses respiratory burst activity in the presence of 3 mM UCA (FIG. 3C). The plot also demonstrates that cis-UCA possesses a more prominent inhibitory activity on the cells in the extracellular pH range 6.1-7.0 than trans-UCA, whereas no difference can be found at above pH 7. When the respiratory burst activity is calculated as a function of the respective intracellular BCECF fluorescence in the same cells, it can be observed that the suppression of respiratory burst activity is related to the decrease in intracellular pH produced by UCA isomers through either extracellular or intracellular acidification (FIG. 8D).

Conclusions

Because UCA is a weak organic acid, the accumulation of UCA inside the cell could regulate the cytosolic pH. This, however, greatly depends on the protonation status of the entering UCA molecules. UCA is a polyprotic acid with two proton-donor moieties, the carboxyl group and the imidazolyl group. The $pK_a$ of the carboxyl group is 4.0 for trans-UCA and 3.3 for cis-UCA (Roberts 1982), from which it follows that practically all UCA molecules are deprotonated at the carboxyl group at pH above 4, according to the Henderson-Hasselbalch Equation (H-H Eq.). Therefore, at the physiological pH range, the protonation status of the imidazolyl group alone determines whether the molecule is able to donate a proton and thereby promote acidification. The imidazolyl $pK_a$ of trans-UCA is 6.1 (Roberts et al. 1982, Krien & Kermici 2000) while for cis-UCA it is markedly higher, 7.0, potentially due to the stabilized tautomeric form of the cis-isomer caused by intramolecular hydrogen bonding between the carboxyl and imidazolyl moieties (Roberts 1982). Consequently, only at pH 7.0 and above, the imidazolyl group of cis-UCA favors deprotonation, whereas trans-UCA is almost completely deprotonated at the same pH. In the present study, this was clearly demonstrable by an experiment where the addition of trans-UCA in HBSS buffer adjusted to pH 6.5 dropped the pH while cis-UCA had almost no effect.

It can be hypothesized that the ability of UCA to acidify cytosol in living cells depends on two major parameters: the pH of the extracellular space and the initial pH of the cytosol. Because UCA is found mainly in the skin, one should consider these two parameters in the context of the physiological environment. It is well known that the human skin has an acid mantle with a surficial pH around 4-6.

When the stratum corneum is stripped layer by layer, the pH increases gradually and, after total removal of the stratum corneum, the pH in the remaining epidermis is about 6.9 (Öhman & Vahlquist, 1994). In deeper layers, the almost neutral pH of the interior body is reached. A recent analysis provides evidence that UCA is the major pH-regulating factor in the human stratum corneum (Krien & Kermici 2000). The majority of UCA resides in the stratum corneum; however, a significant amount of UCA diffuses into and evidently also through the (epi)dermis, because elevated levels of cis-UCA can be detected in the urine within 1-4 h following total-body UVB exposure (Kammayer et al. 1997). Concerning the intracellular environment, pH in the resting neutrophil cytosol is 7.0-7.4, i.e. above the imidazolyl $pK_a$, which suggests that both UCA isomers exist mainly in the deprotonated state in the neutrophil cytosol. At an extracellular pH above the imidazolyl $pK_a$ (6.1 for trans-UCA and 7.0 for cis-UCA), the majority of UCA molecules would be in the deprotonated form and no significant acidification would occur after entering the cytosol. In contrast, at a pH below the imidazolyl $pK_a$'s, UCA would be mainly in the protonated form capable of promoting cytosolic acidification upon cell entry. Moreover, according to the H-H Eq., it can be speculated that the amount of UCA-associated protons and thus the reduction of cytosolic pH would be directly proportional to the transmembrane pH difference between the cytosol and the acidic extracellular environment. To provide experimental support for these hypotheses, we measured the change in cytosolic pH in UCA-treated cells. When extracellular pH was strictly controlled to 7.4 in the incubation mixture i.e. above the $pK_a$'s of imidazolyl group of both UCA isomers, no acidification was seen, as one could expect. On the other hand, at controlled pH 6.5, cis-UCA with imidazolyl $pK_a$ of 7.0 clearly decreased the cytosolic pH while trans-UCA ($pK_a$ 6.1) had only a minor effect. This was also predictable from a calculation using the H-H Equation: at pH 6.5 over 70% of cis-UCA is in protonated and 70% of trans-UCA in the deprotonated state. In theory, lowering the extracellular pH below 6.1 would have allowed us to detect a trans-UCA-induced fall in the cytosolic pH, but it was not possible to test this with the BCECF dye due to its limited operational pH range. Taken together, it is evident that at slightly acidic environment, such as in the upper viable layers of the epidermis, cis-UCA, in effect, can act as a proton shuttle to reduce cytosolic pH. This unique property of UCA originates from a shift in the imidazolyl $pK_a$ caused by changed spatial structure of UCA upon trans-to-cis photoisomerization.

There is no previous data in the scientific and patent literature suggesting that UCA preparations should be formulated at the pH range proposed in the present invention. In the U.S. Pat. No. 5,494,676 by Stab et al. it was described that the photoisomerisation reaction of 1% trans-UCA was performed in a water solution, where the pH was adjusted to 6.9 with NaOH prior the irradiation with an UV-lamp. This solution, containing equal amounts trans-UCA and cis-UCA, was then used to prepare topical O/W-cream formulations. However, the pH of the topical preparations was not pH-adjusted, nor pH-buffered to the preferred pH-range of the present invention.

In conclusion, the present study shows data which, for the first time, may explain the stereospecific action of UCA on immune cells in vivo. Paradoxically, modulation of cell function by UCA seems not to depend directly on stereoisomerism but rather on a subtle but critical change in the acid-base properties of the molecule after photoconversion from the trans- to cis-UCA.

The invention is further illuminated by the following non-restricting Examples.

Examples of Formulations According to the Invention

Gel Composition 1 (% w/w)

| | |
|---|---|
| Cis-urocanic acid | 0.1-10 |
| Carbopol 974 | 1.5 |
| Propylene glycol | 12.5 |
| Buffering agent | 0.01-1 |
| Purified water to | 100 |

Gel Composition 2 (% w/w)

| | |
|---|---|
| Cis-urocanic acid | 0.1-10 |
| Natrosol (hydroxyethylcellulose) | 1.0 |
| Buffering agent | 0.01-1 |
| Purified water to | 100 |

Cream Composition 1 (% w/w)

| Cis-urocanic acid | 0.1-10 |
|---|---|
| Propylene glycol | 50 |
| Cetostearyl alcohol | 15 |
| Sodium lauryl sulfate | 1 |
| Buffering agent | 0.01-1 |
| Purified water to | 100 |

Cream Composition 2 (% w/w)

| Cis-urocanic acid | 0.1-10 |
|---|---|
| Cetostearyl alcohol | 6.75 |
| Propylene glycol | 40 |
| Sodium lauryl sulphate | 0.75 |
| Poloxamer 407 | 1 |
| Mineral oil | 5 |
| Stringy petrolatum 12. | 5 |
| Buffering agent | 0.01-1 |
| Purified water to | 100 |

Ointment Composition (% w/w)

| Cis-urocanic acid | 0.1-10 |
|---|---|
| Mineral oil | 5 |
| Buffering agent | 0.01-1 |
| Petrolatum to | 100 |

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

REFERENCES

Beissert, S., T. Mohammad, H. Toni, A. Lonati, Z. Yan, H. Morrison, and R. D. Granstein. 1997. Regulation of tumor antigen presentation by urocanic acid. *J. Immunol.* 159: 92.

El-Ghorr, A. A., and M. Norval. 1997. The effect of chronic treatment of mice with urocanic acid isomers. *Photochem Photobiol* 65: 866.

Garssen, J., M. Norval, J. Crosby, P. Dortant, and H. Van Loveren. 1999. The role of urocanic acid in UVB-induced suppression of immunity to *Trichinella spiralis* infection in the rat. *Immunology* 96: 298.

Gilmour, J. W., J. P. Vestey, S. George, and M. Norval. 1993. Effect of phototherapy and urocanic acid isomers on natural killer cell function. *J. Invest. Dermatol.* 103:169.

Griffith, R., and R. Dipietro. 1983. An improved preparation of imidazole 4(5)-methanol hydrochloride. *Synthesis* 83:576.

Gruner, S., W. Diezel, H. Stoppe, H. Oesterwitz, and W. Henke. 1992. Inhibition of skin allograft rejection and acute graft-versus-host disease by cis-urocanic acid. *J. Invest. Dermatol.* 98: 459

Hart, P. H., A. Jaksic, G. Swift, M. Norval, A. A. el-Ghorr, and J. J. Finlay-Jones. 1997. Histamine involvement in UVB- and cis-urocanic acid-induced systemic suppression of contact hypersensitivity responses. *Immunology* 91: 601.

Holáň, V., L. Kuffová, A. Zajicová, M. Krulová., M. Filipec, P. Holler, and A. Jančárek. 1998. Urocanic acid enhances IL-10 production in activated CD4+ T cells. *J. Immunol.* 161:3237.

Kanimeyer, A., S. Pavel, S. S. Asghar, J. D. Bos, and M. B. Teunissen. 1997. Prolonged increase of cis-urocanic acid levels in human skin and urine after single total-body ultraviolet exposures. *Photochem. Photobiol.* 65:593.

Kivistö, K., K. Punnonen, J. Toppari, and L. Leino. 1996. Urocanic acid suppresses the activation of human neutrophils in vitro. *Inflammation* 20:451.

Krien, P. M., and M. Kermici. 2000. Evidence for the existence of a self-regulated enzymatic process within the human stratum corneum—an unexpected role for urocanic acid. *J. Invest. Dermatol.* 115:414.

Laihia, J. K., M. Attila, K. Neuvonen, K. Pasanen, L. Tuomisto, and C. T. Jansen. 1998. Urocanic acid binds to GABA but not to histamine ($H_1$, $H_2$, or $H_3$) receptors. *J. Invest. Dermatol.* 111:705.

Lindgren, G., K.-E. Stensjö, and K. Wahlberg. 1980. Synthesis and photocyclization of some 4(5)-arylethenylimidazoles. *J. Heterocyclic. Chem.* 17:679.

Mohammad, T., and H. Morrison. 1991. A general approach to the synthesis of $^{14}C$ labeled acrylic acids. *J. Label. Comp. Radiopharm.* 9:1010.

Moodycliffe, A. M., Bucana, C. D., Kripke, M. L., Norval, M., and Ullrich, S. E. 1996. Differential effects of a monoclonal antibody to cis-urocanic acid on the suppression of delayed and contact hypersensitivity following ultraviolet irradiation. *Immunol.* 157:2891.

Öhman, H., and A. Vahlquist. 1994. In vivo studies concerning a pH gradient in human stratum corneum and upper epidermis. *Acta Derm. Venereol.* 74:375.

Roberts, J. D., C. Yu, C. Flanagan, and T. R. Birdseye. 1982. A nitrogen-15 nuclear magnetic resonance study of the acid-base and tautomeric equilibria of 4-substituted imidazoles and its relevance to the catalytic mechanism of α-lytic protease. *J. Am. Chem. Soc.* 104; 3945.

Rotstein O D, P E Nasmith, and S Grinstein. 1987. The Bacteroides by-product succinic acid inhibits neutrophil respiratory burst by reducing intracellular pH. *Infect. Immun.* 55:864.

Schwarz, T. Ultraviolet radiation-induced tolerance. 1999. *Allergy* 54:1252.

Uksila, J., J. K. Laihia, and C. T. Jansen. 1994. Trans-urocanic acid, a natural constituent of the human skin, inhibits human NK cell activity. *Exp. Dermatol.* 3:61.

Uusi-Oukari, M., S. L. Soini, J. Heikkilä, A. Koivisto, K. Neuvonen, P. Pasanen, S. T. Sinkkonen, J. K. Laihia, C. T. Jansen, and E. R. Korpi. 2000. Stereospecific modulation of $GABA_A$ receptor function by urocanic acid isomers. *Eur. J. Pharmacol.* 400:11.

Wille, J. J. A. F. Kydonieus, and G. F. Murphy. 1999. Cis-urocanic acid induces mast cell degranulation and release of preformed TNF-alpha: A possible mechanism linking UVB and cis-urocanic acid to immunosuppression of contact hypersensitivity. *Skin Pharmacol. Appl. Skin Physiol.* 12:18.

The invention claimed is:

1. A method for treatment of an inflammatory condition, comprising
topically administering a pharmaceutical composition to a person or animal in need thereof, said pharmaceutical composition having a pH in the range of 6.1 to 7.0 and consisting essentially of an effective amount of cis-urocanic acid or a salt thereof, and
reducing inflammation by inhibition of neutrophil activation and function,
wherein said inflammatory condition is ocular inflammation.

2. The method of claim 1, wherein said pharmaceutical composition includes a buffering agent.

3. The method of claim 1, wherein said ocular inflammation is conjunctivitis.

* * * * *